US010314731B2

(12) United States Patent
Kaphingst

(10) Patent No.: US 10,314,731 B2
(45) Date of Patent: Jun. 11, 2019

(54) ORTHOSIS FOR MOVEMENT DAMPING

(75) Inventor: Wieland Kaphingst, Lewistown, NY (US)

(73) Assignee: BAUERFEIND AG (DE)

( * ) Notice: Subject to any disclaimer, the term of this patent is extended or adjusted under 35 U.S.C. 154(b) by 879 days.

(21) Appl. No.: 13/993,501

(22) PCT Filed: Dec. 7, 2011

(86) PCT No.: PCT/EP2011/006146
§ 371 (c)(1),
(2), (4) Date: Jul. 25, 2013

(87) PCT Pub. No.: WO2012/079719
PCT Pub. Date: Jun. 21, 2012

(65) Prior Publication Data
US 2013/0296757 A1    Nov. 7, 2013

Related U.S. Application Data

(60) Provisional application No. 61/423,113, filed on Dec. 15, 2010, provisional application No. 61/467,463, filed on Mar. 25, 2011.

(30) Foreign Application Priority Data

Dec. 15, 2010   (DE) .......................... 10 2010 054 579
Mar. 25, 2011   (DE) .......................... 10 2011 016 144

(51) Int. Cl.
*A61F 5/01*        (2006.01)
(52) U.S. Cl.
CPC ...... *A61F 5/013* (2013.01); *A61F 2005/0167* (2013.01); *A61F 2005/0169* (2013.01)

(58) Field of Classification Search
CPC .... A61F 5/0123; A61F 5/0118; A61F 5/0106; A61F 5/05841; A61F 5/0585;
(Continued)

(56) References Cited

U.S. PATENT DOCUMENTS 1,622,211 A * 3/1927 Sheehan ............ A63B 71/1225
                                                       2/22
2,068,251 A * 1/1937 Ullrich ................. A43B 7/1495
                                                      36/170
(Continued)

FOREIGN PATENT DOCUMENTS

WO   WO 2010/087899 A2    8/2010

OTHER PUBLICATIONS

International Preliminary Report on Patentability and the Written Opinion of the International Searching Authority dated Jun. 18, 2013 issued in corresponding PCT International Application No. PCT/EP2011/006146.
(Continued)

*Primary Examiner* — Kari K Rodriquez
*Assistant Examiner* — Camtu T Nguyen
(74) *Attorney, Agent, or Firm* — Ostrolenk Faber LLP

(57) ABSTRACT

An orthosis is supplied to the human or animal body in order to perform a supporting or movement-guiding function. The orthosis here damps or limits the flexion or extension movement of a limb joint, such as the elbow joint, knee joint, etc., and describes the prophylactic and therapeutic use of the orthosis. The manner of its attachment and placement is described.

15 Claims, 11 Drawing Sheets

(58) Field of Classification Search
CPC .. A61F 5/05866; A61F 5/0127; A61F 5/0111; A61F 5/14; A61F 5/0113; A61F 5/05858; A61F 5/05875; A61F 5/013
USPC .................................. 602/24, 26–27, 28, 20
See application file for complete search history.

(56) References Cited

U.S. PATENT DOCUMENTS

| | | | | |
|---|---|---|---|---|
| 2,195,024 | A * | 3/1940 | Bullock | A61F 5/0125 2/22 |
| 2,407,556 | A * | 9/1946 | Kleven | A43B 3/10 36/12 |
| 3,387,305 | A * | 6/1968 | Shafer | A61F 5/0125 2/22 |
| 3,785,371 | A * | 1/1974 | Lewis | A61F 5/0118 602/20 |
| 4,550,721 | A * | 11/1985 | Michel | A43B 7/00 602/27 |
| 4,700,698 | A * | 10/1987 | Kleylein | A61F 13/062 602/26 |
| 4,854,308 | A * | 8/1989 | Drillio | A61F 5/0123 602/16 |
| 5,063,916 | A | 11/1991 | France et al. | |
| 5,167,612 | A * | 12/1992 | Bonutti | A61F 5/0123 601/33 |
| 5,367,794 | A * | 11/1994 | Adelstein | A43B 5/185 36/135 |
| 7,458,950 | B1 * | 12/2008 | Ivany | A43B 7/14 36/136 |
| 2003/0144620 | A1 * | 7/2003 | Sieller | A61F 5/0125 602/5 |
| 2005/0075594 | A1 * | 4/2005 | Hepburn | A61F 5/0125 602/16 |

OTHER PUBLICATIONS

International Search Report dated Mar. 22, 2012 issued in corresponding International patent application No. PCT/EP2011/006146.

* cited by examiner

ORTHOSIS FOR MOVEMENT DAMPING

CROSS-REFERENCE TO RELATED APPLICATIONS

The present application is a 35 U.S.C. §§ 371 national phase conversion of PCT/EP2011/006146, filed Dec. 7, 2011, which claims priority of U.S. Provisional Application No. 61/423,113, filed Dec. 15, 2010, German Patent Application No. 10 2010 054 579.1, filed Dec. 15, 2010, German Patent Application No. 10 2011 016 144.9, filed Mar. 25, 2011, and U.S. Provisional Application No. 61/467,463, filed Mar. 25, 2011 the contents of which are incorporated by reference herein. The PCT International Application was published in the English language.

The invention relates to the technical field of orthoses and medical aids that are applied to the human or animal body in order to perform a supporting or movement-guiding function. The invention specifically makes available an orthosis for damping or limiting the flexion or extension movement of a limb joint, such as the elbow joint, knee joint, etc., and the prophylactic and therapeutic use of said orthosis.

Orthoses for supporting joints and for controlling the movement of joints, that is to say for controlling the kinematics and kinetics, are known. The aim of these orthoses is basically to limit the movement amplitude of a flexion or extension movement performed at the joint, above all in order to avoid hyperextension of the joint and the associated disadvantageous overextension of the joint apparatus, particularly of the ligaments. This is especially expedient as part of a measure for immobilizing joints in postoperative states, and also in prophylaxis for preventing sports injuries in types of sports where the risk of hyperextension of a joint and of the associated damage is reduced. In baseball or softball, for example, the player throwing the ball (thrower, pitcher) is exposed to the risk that, when performing the throw, the elbow joint is overextended and, as a result, in particular the medial collateral ligament, which attaches to the medial epicondyle of the elbow, is damaged or completely tears. For example, 26% of children playing the sports and 58% of the adolescent players have serious problems in the area of the medial elbow, which problems are associated with damage to the elbow joint in the area of the medial epicondyle and of the collateral ligament. This damage can often still be compensated by surgical measures such as UCLR ("Tommy John Surgery").

It can also be advantageous to damp the flexion of a joint and limit the amplitude of the flexion movement. There are traumatic or pathological states in which the person affected is no longer able to extend the hand at the wrist. This is generally known, for example, in patients who have suffered a stroke, and who have to live with what is called flaccid paralysis of the extensors of the hand, also called wrist drop. A hand that cannot be lifted at the wrist when things are to be gripped is entirely unfunctional. Orthoses that bring a hand to the so-called functional position allow the affected person to actively use the paralyzed hand again to a limited extent, and they are therefore found to be a great source of help.

Therefore, an excessive flexion or extension movement or valgus movement of the joint should expediently be limited by external measures. Known orthoses that can be used to limit the movement of a limb joint usually have rigid end-stops or flexurally stiff elements for limiting the movement. Alternatively, resiliently elastic elements are provided. However, both the rigid end-stop and also the resiliently elastic elements force the limb into non-physiological movement patterns that are felt particularly inconvenient especially by the user, for example a sports person with considerable movement amplitudes. The acceptance of such orthoses is therefore very limited.

Moreover, because of the great acceleration forces that have to be taken up, known orthoses often have solid constructions which, during use, particularly in sport, are a source of inconvenience, and, particularly in certain team sports, they cannot be worn on account of the risk of injury to other players. In known orthoses, the measures for fixing the orthosis to the limb joint are disadvantageous.

If the orthosis is to perform its movement-limiting function, it must be fitted firmly on the joint. This causes constrictions which, over the long term, disturb the circulation of blood in the underlying muscles or soft-tissue parts. The person wearing the orthosis experiences a constant feeling of pressure, which has the disadvantage of preventing adequate proprioceptive feedback of the limitation of the extension movement.

In known orthoses with flexurally stiff elements and fixed movement limitation, the latter has the disadvantage of having an abrupt onset, which leads to non-physiological movement patterns. The user therefore often avoids performing the movement, even to the permitted extent, so as to avoid the abrupt movement limitation caused by the orthosis.

The object of the invention is to make available an improved orthosis for damping or limiting the movement, in particular the extension movement and/or flexion movement, of a limb joint, which orthosis partially or completely overcomes the disadvantages of the prior art, has in particular a simple construction that does not cause inconvenience when being worn, and at the same time limits the joint movement according to the physiological model and permits proprioceptive feedback of the movement.

The invention achieves this object by making available an orthosis for damping or limiting the movement, degree of movement or amplitude of movement of a limb joint, which orthosis has, according to the invention, at least one cuff that engages around the limb below the joint (distally or proximally) and that is coupled to at least one abutment that can be applied to the limb above the joint (proximally or distally). At least one tensioning band extends from the at least one proximal abutment to the at least one cuff and is intended to connect the abutment and cuff with a force fit and, for this purpose, can be connected to abutment and cuff with a force fit. The cuff has at least one pressure-initiating portion, which can preferably act on soft-tissue parts located in the area of the cuff. According to the invention, the at least one pressure-initiating portion of the cuff is coupled to the at least one tensioning band, and the tensioning band is designed in such a way that it can be stretched by the extension movement of the limb when the orthosis is in place, in order thereby to exert compression, via the at least one pressure-initiating portion, on at least one soft-tissue area of the limb lying under the at least one pressure-initiating portion. In this way, according to the invention, the joint movement is damped or limited in a controlled manner, without the disadvantages that are known from known orthoses.

It will be appreciated that the orientation of the orthosis on the joint can also be configured in reverse, depending on requirements. The cuff imparting the pressure initiation into a soft-tissue area then lies above (proximal to) the joint, and the abutment lies below (distal to) the joint. The orientation of the orthosis depends especially on the anatomical circumstances of the joint, particularly on where, in the area of the joint, a soft-tissue part, particularly a muscle belly, can be located that is suitable for pressure initiation and damping.

The invention therefore proposes that the elastic and damping properties of the body tissue itself should be used for limiting the extension movement. By diverting the change in length during the joint movement to soft-tissue parts in the area of the joint, a physiological damping can be achieved that is similar to the physiological limitation afforded by the apparatus supporting the joint. Whereas known orthoses with a fixed end-stop cause an abrupt increase in force as soon as this end-stop is reached, the movement limitation imparted according to the invention via the soft-tissue part starts "gently" toward the end of the movement. At the same time, a proprioceptive feedback on the limitation of the extension movement is advantageously imparted via the soft-tissue part. Compared to other known orthoses that use resiliently elastic elements for limiting=movement, the limitation imparted according to the invention via soft-tissue parts has the advantage of a non-linear curve, which shows action only toward the end of the movement. By contrast, a resiliently elastic limitation of movement has a Hooke curve, which already shows force action at the start of the movement.

Therefore, the orthosis is primarily used according to the invention for controlling the extent of the rotatory movement about the transverse horizontal axis of the joint. Moreover, it is also used as a system for controlling the movement force and movement moment at the joint end-stop when the movement has been completed. In this way, the orthosis according to the invention prevents an undamped, abrupt end-stop at the completion of the movement, which abrupt end-stop can have the disadvantage of leading to a high impulse and, consequently, to damage in the joint apparatus. The damping function imparted according to the invention reduces the acceleration forces for stopping the movement at the end of the performed joint movement. This is particularly effective in limiting the extension movement, for example for a throw (elbow joint) or kick (knee joint).

Besides limiting the extension movement at the joint, the orthosis according to the invention also makes it possible in particular to additionally limit the rotation movement of the distal limb (that is to say forearm, lower leg, palm of the hand), particularly the outward rotation (supination). In this way, the joint and muscle apparatus imparting this rotation movement can be protected in particular, and injuries caused by excessive rotation movement, especially supination trauma, can be avoided.

Without wishing to be bound to the following theory, the soft-tissue-imparted movement limitation, which leads to moderate intermittent compression, can be compared to the compression of water cushions in elastic casings. The biological cells in the soft-tissue part, particularly in a muscle bundle, thus have their function converted to a quasi hydraulic damper in a resiliently elastic housing. According to the invention, this damping is transmitted to the soft-tissue parts by means of the tensioning elements and damps the end-stop. By the increasingly damping muscle compression, the final movement limitation is achieved technically, mechanically and free of jolts, with a simultaneous proprioceptive feedback function for the user. Without wishing to be bound to this theory, the affected mechanoreceptors of the soft-tissue part fire during the soft-tissue-imparted movement limitation according to the invention and thus permit a neurophysiological feedback essentially analogous to the pressure variable and thus essentially analogous to the angle setting of the joint.

The advantage of this orthosis over the prior art lies in using the compressive and sensory properties of tissue in order to control the passive movement of a motor-paralyzed limb. After a settling-in period, the user is thus provided with a natural, proprioceptive feedback function.

The orthosis according to the invention is primarily described herein using the example of an elbow orthosis. In the case of an elbow orthosis, the main aim is to prevent the overextension of the ligaments caused by sports injuries of the kind that occur in baseball or tennis. An example is the collateral ligament on the medial epicondyle of the elbow. In this case, an orthosis according to the invention designed as an elbow orthosis controls the extension or hyperextension and the varus or valgus movement in the radiohumeral joint (elbow joint). The soft-tissue-imparted extension limitation according to the invention is preferably achieved using the muscle belly of the flexor and extensor groups of the hand in the forearm. In a particular embodiment of the orthosis according to the invention, it is a so-called "pitcher elbow" orthosis, which can be used especially for baseball.

While the structure and the principle of action of the orthosis according to the invention are mainly described herein using the example of an elbow orthosis limiting the extension movement, the invention is not limited thereto. It can instead be employed in all areas in which orthoses have hitherto been used for the therapeutic and prophylactic control of the kinematics and kinetics of limb joints. Examples of these are orthoses in the area of the foot, for example for controlling the downwardly directed joint movement of the front of the foot in cases of foot-drop caused by flaccid paralysis. The movement of the talotibial joint (ankle joint) is limited in this case. The soft-tissue-imparted movement limitation is preferably achieved using the muscle belly of the calf (musculus gastrocnemius and musculus soleus).

Another example is the control of the extension movement in the tibiofemoral joint (knee joint). The aim here is to prevent a hard extension end-stop, caused for example by partial paralysis or weakness in the joint apparatus, or a hyperextension of the knee joint. The soft-tissue-imparted extension limitation according to the invention is preferably achieved using the calf (musculus gastrocnemius and musculus soleus) and/or the thigh (musculus quadriceps femoris) and/or extensor/adductor groups of the hip. Alternatively, the orthosis according to the invention is designed as a hand orthosis, in particular for controlling a downwardly directed flexion in the radiocarpal joint (wrist), for example in cases of wrist drop caused by paralysis. The soft-tissue-imparted flexion limitation according to the invention is achieved using the flexor and/or extensor groups of the hand.

In a particular embodiment of the orthosis according to the invention, the at least one cuff has at least two mutually opposite pressure-initiating portions. These pressure-initiating portions are each coupled, or can be coupled, to at least one tensioning band. In this way, in particular a substantially symmetrical pressure initiation is permitted in the area of the soft-tissue part. At the same time, this symmetry of the acting force counteracts a displacement of the orthosis during use. In a particular embodiment, therefore, at least two tensioning bands are provided which extend substantially symmetrically with respect to each other, particularly starting from the abutment, crosswise to the at least two mutually opposite pressure-initiating portions of the cuff.

In a preferred embodiment, the at least one tensioning band, starting from the abutment proximal to the joint, extends on a first side (for example the inner side) of the limb, crosses the longitudinal axis of the limb and, distal to the joint, ends on the opposite second side (for example the outer side) of the limb in the area of the pressure-initiating portion on this second side of the cuff. Accordingly, preferably at least a second tensioning band is provided extending symmetrically thereto. Therefore, this second tensioning band, starting from the abutment proximal to the joint, extends in particular on the opposite second side (for example the outer side) of the limb, crosses the longitudinal axis of the limb and, distal to the joint, ends on the first side (for example the inner side) of the limb in the area of the pressure-initiating portion on the first side of the cuff.

In a particular embodiment, at least one tensioning band can be connected releasably to the cuff in the area of the associated pressure-initiating portion thereof and thus can be adjusted in terms of its effective length. In this way, the degree of the movement limitation or the extent of the still permissible joint movement can be predetermined. With a short tensioning band, the extension limitation begins even at quite a small angle of extension. With a long tensioning band, the movement limitation finally begins only when the joint has been fully extended or flexed. It will be appreciated that, by adjusting the effective length of the tensioning band, it is also possible to completely cancel the limitation of the joint movement temporarily. This is particularly useful and expedient for adaptation to certain movement states, for example sitting, walking, sports activities, training, therapy, etc. Provision is made in particular that the tensioning length can be individually adjusted by the treating physician or orthopedic specialist according to the indication and the aim of treatment. Alternatively or in addition, the tensioning length can also be adjusted by the user. For example, one or more markings, color codes, symbols can be provided here on the tensioning band or in the area where the tensioning band is fixed to the cuff, and these make adjustment easier for the user and, in particular, permit independent adaptation to the movement conditions and/or to a therapy plan.

In a particular embodiment, at least one tension diverter is provided particularly on the at least one distal cuff, via which tension diverter the tensioning band is guided. The tension diverter allows the soft-tissue-imparted extension limitation to be further improved, since the tension that can be generated on the tensioning band during execution of the extension movement is deflected in the area of the distal cuff via the at least one tension diverter and is distributed in particular to two mutually opposite pressure-initiating portions, in such a way that it is possible to achieve a direct compression of the soft-tissue part provided for damping the joint movement. For this purpose, provision is made in particular that the at least one tensioning band, starting from the proximal abutment, is guided via the at least one tension diverter in the area of one pressure-initiating portion to an opposite pressure-initiating portion and is anchored there. The tension diverter is configured in particular as an eyelet through which the tensioning band is guided. Alternatively, the tension diverter is configured as a mounted roller, in order additionally to minimize the frictional forces in the area of the tension diverter. The person skilled in the art is familiar with corresponding designs of tension diverters in the field of orthoses and can use these to realize the function provided according to the invention.

In an alternative variant thereof, the tension diverter of the tensioning band is designed, between the two mutually opposite pressure-initiating portions, in the form of a single or multiple pulley, in order to even out the force initiation in the area of the soft-tissue part for the extension limitation and/or to adapt the force to specific uses of the movement limitation. This may be necessary in particular in orthoses for use in sports, in order to allow the movement limitation to start "gently but surely" only at the end of the joint movement and in order to take up the high forces that occur in sports activities. In addition, other designs with mechanical tension diverters are provided which permit adaptation of the response behavior, that is to say of the non-linear damping imparted via the soft-tissue part.

In order to achieve the function according to the invention, the invention proposes that the at least one tensioning band is made from a substantially inelastic flexible material. The person skilled in the art is familiar with flexible materials that can be used to design a cuff according to the invention. These are in particular inelastic flexible materials such as polymer, polymer/fiber composite material or woven fabric.

In another embodiment, the at least one tensioning band or at least one of the tensioning bands is made partially or completely from an elastic material. In this particular embodiment, the damping effect can be influenced in a deliberate manner, in particular avoiding, force peaks. In a particular variant of this particular embodiment, provision is additionally made that the elastic tensioning band is designed to permit training of the muscles of the joint apparatus.

The pressure initiation imparted, according to the invention via the elastic tensioning band, to soft-tissue parts at the at least one pressure-initiating portion connected to the elastic tensioning band advantageously ensures a proprioceptive feedback, which allows the user to perform specific training. In this particular embodiment, provision can be made that the orthosis itself does not impart any substantial extension limitation, but instead, by means of the proprioceptive feedback, "teaches" the user the movement, particularly in the area of the end position of the joint. This embodiment of the orthosis can be used particularly in sports training and also in particular in the postoperative treatment of injuries to the joint apparatus.

In a particular embodiment, provision is additionally made that, in the context of the soft-tissue-imparted extension limitation, the pressure initiation on the soft-tissue part is specifically used for the intermittent compression of the tissue. In this way, for example, the blood flow and in particular the biological venous pump of the circulatory system are stimulated. This is of particular interest in connection with the training of certain muscle parts connected to the joint. To this extent, the orthosis according to the invention, in this embodiment, can also serve as a training device which, during the training movement, permits an active massage of the underlying soft-tissue part, in particular of muscle tissue.

In order to impart the force initiation into the soft-tissue part lying under the at least one pressure-initiating portion of the distal cuff, a pad or pressure plate oriented toward the soft-tissue part of the limb is in particular provided. This can additionally be specifically designed with "massage points" in order to improve the proprioceptive feedback. Alternatively or in addition, the pad or pressure plate is adapted in shape to the outer shape of the soft-tissue part. Generally, the soft-tissue part used for the damping is muscle tissue, particularly a bundle of different muscle strands. A pad or pressure plate provided in this particular embodiment can be designed such that, within the muscle pack, it specifically allows pressure to be introduced into certain muscle sections or muscle groups. At the same time, provision can be made that the pad or pressure plate specifically applies pressure to the nerve fibers extending through the soft-tissue part or alternatively avoids applying pressure thereto. This can be chosen depending on the area of use or the aim of treatment, in order in particular to improve the proprioceptive feedback or to adapt the latter to the movement situation.

In a particular embodiment, the abutment is formed by at least one tensioning band encircling the limb proximal to the joint. In this particular embodiment, therefore, the tensioning band itself basically forms the abutment. In this case, provision is preferably made that the tensioning band is widened in the area of contact with the limb in order to even out the frictional connection. In a particular variant, a pad or pressure plate additionally provided between tensioning band and limb establishes the frictional connection between the abutment, designed as tensioning band, and the limb proximal to the joint. The frictional connection can be established in a specific manner by means of the pad or pressure plate provided in this variant. In particular, this permits fixing and positioning of the orthosis. At the same time, the tissue structures lying underneath the abutment are protected mechanically.

In another embodiment, the abutment is designed as a non-deformable shell that encloses the rear portion of the limb proximal to the joint. The at least one tensioning band is fixed or can be fixed to this abutment.

In a particular embodiment, the distal cuff is designed such that it encloses the limb, and additionally the soft-tissue structure provided for the soft-tissue-imparted extension limitation according to the invention, at least about a semicircle, that is to say at least by half, but preferably almost completely. In a particular variant, the cuff for this purpose has at least one lower, non-deformable portion. The latter essentially forms the base of the cuff and bears on the distal portion of the limb outside the area of the soft-tissue part. In this variant, the cuff additionally has at least one upper, flexible portion. The at least one upper flexible portion of the cuff is formed in the area of the soft-tissue part. The at least one pressure-initiating portion, which can be brought into contact with the soft-tissue part, if appropriate via at least one pad or pressure plate, is provided on the at least one upper flexible portion. The flexible design, at least of the upper portion of the cuff, has the effect that, by means of the tension generated according to the invention on the tensioning band during the extension movement, the at least one pressure-initiating portion is able, by virtue of the tension on the tensioning band, to move toward the soft-tissue part and exert pressure there.

The flexible design of the upper portion of the cuff can also be obtained if a substantially non-flexible upper portion is connected to the substantially non-deformable lower portion in an articulated manner. For this purpose, a bead or a so-called film hinge is preferably provided between lower portion and upper portion. In an alternative embodiment, instead of or in addition to the flexible upper portion, the lower portion is provided with a flexible connection that divides the cuff particularly at the center and that connects the two resulting cuff halves to each other in an articulated manner. A bead or a so-called film hinge is in particular provided for this purpose.

In one embodiment, the entire cuff is made of flexible material. The person skilled in the art is familiar with flexible materials that can be used to form a cuff according to the invention. These are in particular inelastic flexible materials such as polymer, polymer/fiber composite material or woven fabric. In particular embodiments, this material can be used for the abutment. Cuff and abutment are preferably made of the same material. Cuff and abutment can be made, partially or completely, from stiff materials, such as thermoplastic polyolefins, less stiff materials, such as thermoplastic elastomers, or very flexible materials, such as suitably adapted polyurethanes, cellular foams or silicones. Injection molding techniques, thermoplastic forming techniques or casting techniques can be used; the person skilled in the art is familiar with suitable material variants and also with suitable production techniques.

In a particular embodiment, distal cuff and proximal abutment are designed as an integral unit. In a particular variant, cuff and abutment are formed in one piece as a unit. In this case, provision is in particular made that cuff and abutment, at least in the area of the joint, are coupled to each other flexibly, but with a force fit, and substantially inelastically in the manner of a single-axis or multi-axis hinge. In another particular variant, cuff and abutment are designed separately from each other, and they are connected to each other in an articulated manner and with a force fit via at least one separate hinge or at least one separate hinge coupling. In a simple variant, the hinge is a single-axis hinge located in the area of the elbow joint. In a preferred embodiment, the hinge is in the form of a flexible hinge coupling. The hinge coupling permits a flexible force-fit connection in the manner of a multi-axis hinge, which is better able to follow the anatomical joint movement. Such flexible hinge couplings are known per se. In a particular embodiment, they have an outer substantially rubber-elastic sheath, with an inner flexible and substantially inelastic core, which is formed from inelastic fiber, for example.

In a particular embodiment, the orthosis is designed as part of a so-called soft good orthosis or can be fitted on such. In this case, a textile knit is in particular provided, which is stocking-shaped, for example, and can thus be pulled over the joint. The orthosis according to the invention can be fixed on the textile knit in order in this way to form a functional orthosis unit. The textile knit itself can advantageously perform a joint-supporting orthosis function. Depending on the aim of treatment and on the state of movement, the orthosis according to the invention can, if necessary, be fitted onto the textile orthosis for supporting the extension limitation. Measures known per se can be used for the connection between textile knit and orthosis according to the invention. These measures include, in particular, hook-and-loop connections and buttons.

In a particular embodiment, the orthosis according to the invention is designed as an integral part of a textile knit orthosis. For this purpose, provision is made in particular that the individual elements of the orthosis according to the invention, particularly the distal cuff and the proximal abutment and also the tensioning band, are worked, particularly as mechanically inelastic plates or films or fabric, into the textile knit orthosis or are mounted thereon and connected thereto. The connections between the orthosis elements and the textile knit are made in a manner known per se. Provision is made in particular for welding, stitching and/or adhesive bonding. In an alternative embodiment, at least one orthosis element is injected directly onto the textile knit and thus integrally connected to the latter. In one variant of the invention, the textile knit carries the preferably provided pad(s). These are in particular arranged in the area of the pressure-initiating portions and/or in the area of the abutment.

In other particular designs of the orthosis according to the invention, particularly in the embodiment thereof as an elbow orthosis, provision is made that the abutment is in the form of a rigid half-shell, on which in each case a condyle bed is formed. This condyle bed makes it possible in particular to fix the abutment shell in position on the joint.

Provision can further be made that the cheeks or wings of the abutment engaging round the upper limb are connected about the circumference of the limb to a strap in order to better fix the abutment on the upper limb. In use, the strap is closed after application. Instead of a strap, it is possible, in an alternative embodiment, to provide a multiplicity of eyelets on each of the mutually opposite cheeks of the abutment, and the abutment can be fixed to the limb in the manner of a shoelace.

Particularly on a non-deformable abutment shell, a clamp mechanism can also be provided for adjusting the length of the tensioning band. The clamp mechanism is designed, for example, as a self-inhibiting roll-up mechanism, which is adjustable in particular by locking, in order to set or activate the movement limitation according to requirements.

Particularly on a non-deformable abutment shell, the tensioning band can be guided on an additional tension diverter anchored there, in order to orient the tensioning direction to the lower cuff, so as to support the function according to the invention.

In a particular design, in order to divert and anchor the tensioning band on the lower cuff, both sides of the wings of the cuff are provided with a multiplicity of eyelets through which the tensioning band can be guided, particularly in the form of a shoelace. Provision is made that, when the tensioning band is tensioned according to the invention, the lower cuff bears more tightly on the lower limb, in order to impart the movement damping to the muscle belly of the limb.

In designs according to the invention, the lower cuff is in one piece and engages round the lower limb for the most part. The lower cuff is made from a non-deformable, flexible material. In a particular embodiment, the lower cuff is a non-deformable knit, which is less elastic than an underlying base knit of the bandage stocking of the orthosis. In a variant thereof, the lower cuff is formed by a substantially inelastic flexible knit. In another embodiment, the lower cuff is designed as a non-deformable, flexible polymer film, which is fitted on the underlying base knit, particularly being adhesively bonded, sewn or welded thereto.

Provision is made in particular that the lower cuff, in the form engaging round the limb, is designed narrowing in the direction away from the joint. This narrowing or conical design of the lower cuff advantageously avoids a situation where, upon tensioning according to the invention, the lower cuff slips past the muscle belly of the lower limb and the movement damping intended according to the invention does not fully occur. The conical design means that, when tension is applied, the cuff runs onto the muscle belly of the lower limb and the movement damping is imparted by the run-on movement.

In alternative variants, the tensioning band is partially or completely designed as a tensioning cable of substantially circular cross section. In a preferred variant thereof, the tensioning cable is a steel cable encased in plastic. In the case where the tensioning band is designed partially as a tensioning cable, the fabric of the tensioning band is coupled at the ends thereof to a tensioning cable in a manner known per se, for example by riveting or sewing. The partial or complete design of the tensioning band as a tensioning cable has in particular the advantage that it can be better guided in diverter eyelets or rolled up in a clamp mechanism. In one variant, the tensioning cable extends inside a protective textile sleeve. In one variant, the tensioning cable extends at least partially in tensioning cable channels inside the knit.

In particular embodiments, an inelastic strapping is formed on the base knit of the bandage in the distal area, that is to say at the lower end thereof, as a result of which the orthosis can additionally be secured to the lower limb. The strapping is preferably arranged below the muscle bellies of the lower limb. The additional securing by means of the strapping additionally avoids the lower cuff of the orthosis slipping, since the strapping takes up the shearing forces that occur during use. In a particular variant, the strapping consists of a knit that is less flexible than the base knit lying underneath. The strapping is fitted on the base knit preferably by sewing and also by a hook-and-loop connection. The strapping is preferably guided in the base knit via a so-called thread-in loop and fixed in a manner known per se, in particular by a hook-and-loop connection. In a particular variant, the strapping is interrupted on two mutually opposite sides along the periphery of the strapping. A lace can be provided in one interruption, as a result of which the effective length of the strapping can be preset. In the opposite interruption of the strapping, the above-described strap closure with thread-in loop for repeated application is formed.

In the proximal area of the knit, that is to say particularly at the upper end thereof, an adhesive band can additionally be provided. This adhesive band has adhesive structures, in particular silicone, directed particularly toward the limb. In this way, the position of the orthosis on the limb can be additionally secured. Provision is particularly made that, when the orthosis knit is being applied, the adhesive band is turned back in order to initially suppress the adhesive action. In the applied state, the adhesive band is turned forward and then lies adhesively on the skin.

In the particular embodiment as an elbow orthosis, the structure according to the invention permits the prophylaxis and/or therapy of injuries or irritation to the medial epicondyle of the elbow joint, particularly of medial epicondylitis. The invention thus also covers the medical use of the orthosis according to the invention for the prophylaxis and/or therapy of medial epicondylitis and of diseases and disturbances associated therewith. In particular, wearing the orthosis according to the invention can prevent injury to the ulnar collateral ligament, which attaches to the medial epicondyle. The invention therefore also relates to the medical use of the orthosis according to the invention for the prophylaxis and/or therapy of an injury to the ulnar collateral ligament and of diseases or disturbances associated therewith.

The invention also relates to the use of the orthosis for the prophylaxis and/or therapy of supination trauma to a limb joint, particularly the elbow joint. The invention is described in the following examples on the basis of an elbow orthosis and a wrist orthosis of analogous design, without the invention being limited thereto.

In the figures.

Figure 1:
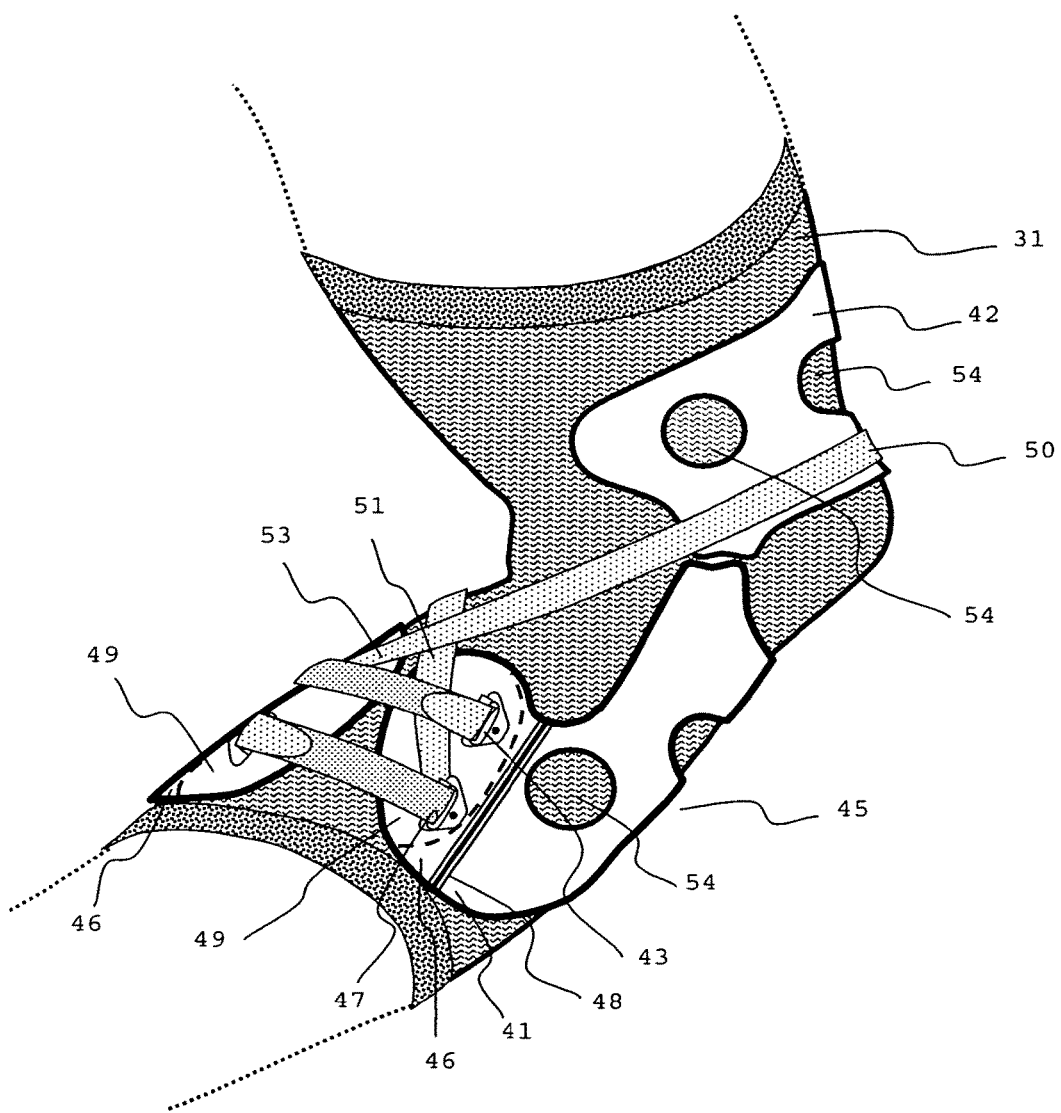
FIG. 1 shows an orthosis according to the invention designed as an elbow orthosis for extension damping.

The elbow orthosis according to the invention shown in FIGS. 1, 3, 4 and 5 is provided on a stocking-like textile knit (31) and has a lower cuff (45), which is connected by a flexible hinge coupling (44) to an abutment (42) above the joint. The cuff (45) is shell-shaped and engages around the forearm, at least around approximately three quarters of the total circumference thereof. In one embodiment, the lower cuff (45) has a non-deformable portion (41) and flexible portions (46). The flexible portions (46) support or form the pressure-initiating portions (49). The flexible portions (46) are connected to the non-deformable portion (41) of the cuff (45) in an articulated manner, preferably via beads or film hinges (48). Alternatively, flexible portions (46) and non-deformable portion (41) are formed seamlessly in one piece and without a bead (48). In this alternative embodiment, flexibility can be achieved by reduced material thickness or by a change in the composition of the material in the area of the flexible portions (46) of the cuff.

Extending around the abutment (42) is at least one tensioning band (50), of which the ends cross in the area of or below the joint and run out in a medial-lateral portion (53) and a lateral-medial portion (51) in relation to the anatomical structure of the elbow. These portions of the tensioning band (50) are fixed with a force fit in eyelets (43) in the area of the pressure-initiating portions (49). In one embodiment, the ends of the tensioning bands can be fixed there in a manner adjustable in length by means of hook-and-loop tongues known per se. Tension diverters (47) can be additionally provided for anchoring. In the tension diverters (47), the ends of the tensioning bands, here shown for tensioning band (51), are guided from the pressure-initiating portion (49) on one side to the opposite pressure-initiating portion on the other side and are anchored releasably there in an eyelet (43). For clearer illustration, the tensioning band (53) is shown in the opened (released) state in FIG. 4. The hook-and-loop closure (58) is additionally shown on the tensioning band (53) in FIG. 4. A flexible, preferably inelastic coupling element (44) is also provided, which connects cuff (45) and abutment (42) to each other in an articulated manner and with a force fit. The figure additionally shows apertures (54), which can optionally be provided to save material, to provide ventilation and/or to influence the material properties in a manner known per se.

Figure 2:
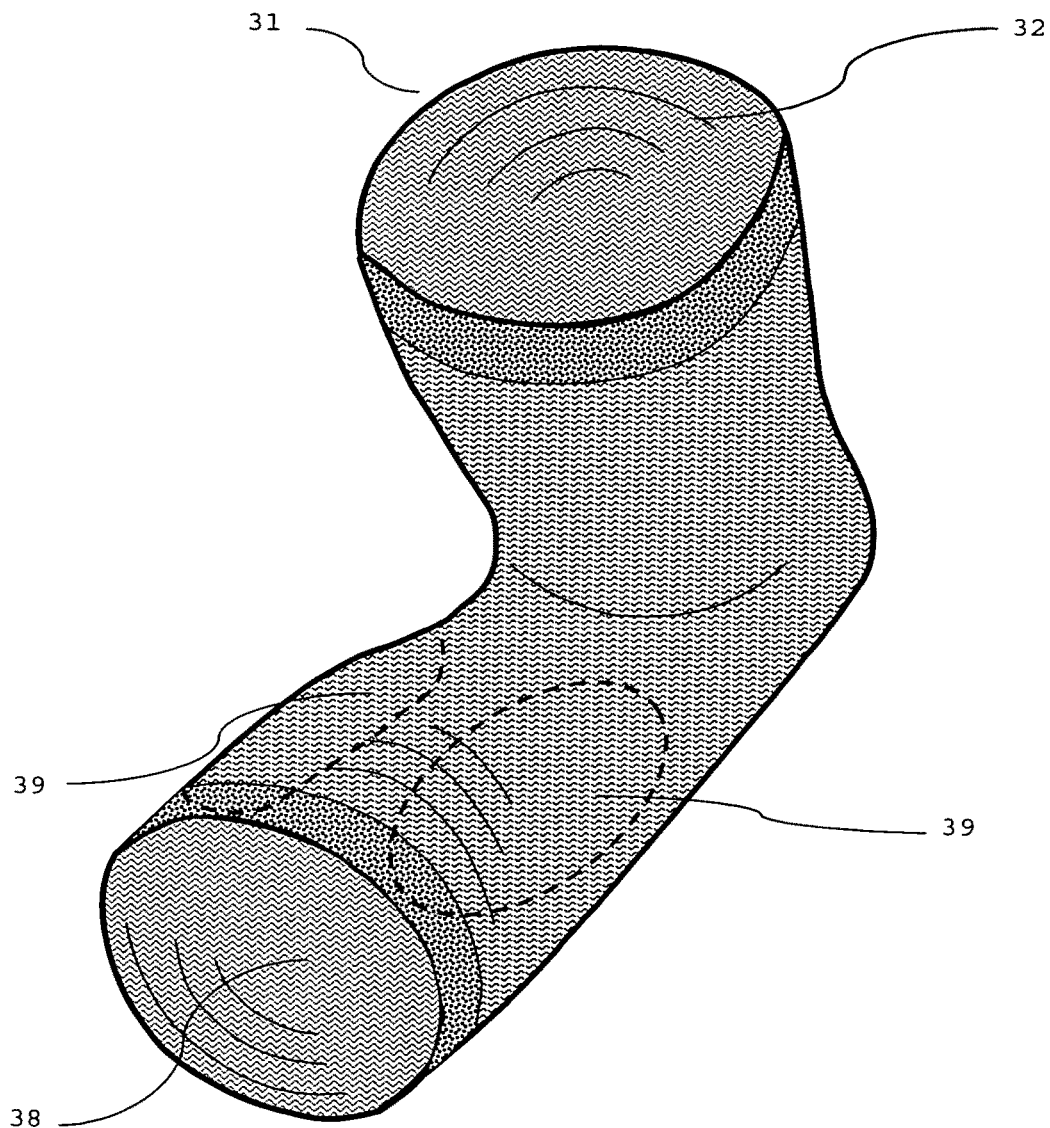
FIG. 2 shows a textile knit according to FIG. 1 in detail.

The textile knit (31) from FIG. 1 is shown in detail in associated FIG. 2. It is stocking-shaped and has an upper (proximal) opening (32) for the upper arm, a pad (37) arranged in the area of the medial muscle belly, a lower (distal) opening (38) for the forearm, and pads (39) arranged in the area of the lateral muscle belly of the forearm. With the orthosis according to the invention equipped as in FIG. 1, 3, 4 or 5, the pads (39) are expediently arranged directly under the pressure-initiating portions (49) in order to ensure that the pressure initiation required for the soft-tissue-imparted extension limitation is conveyed into the underlying muscle belly.

Figure 3:
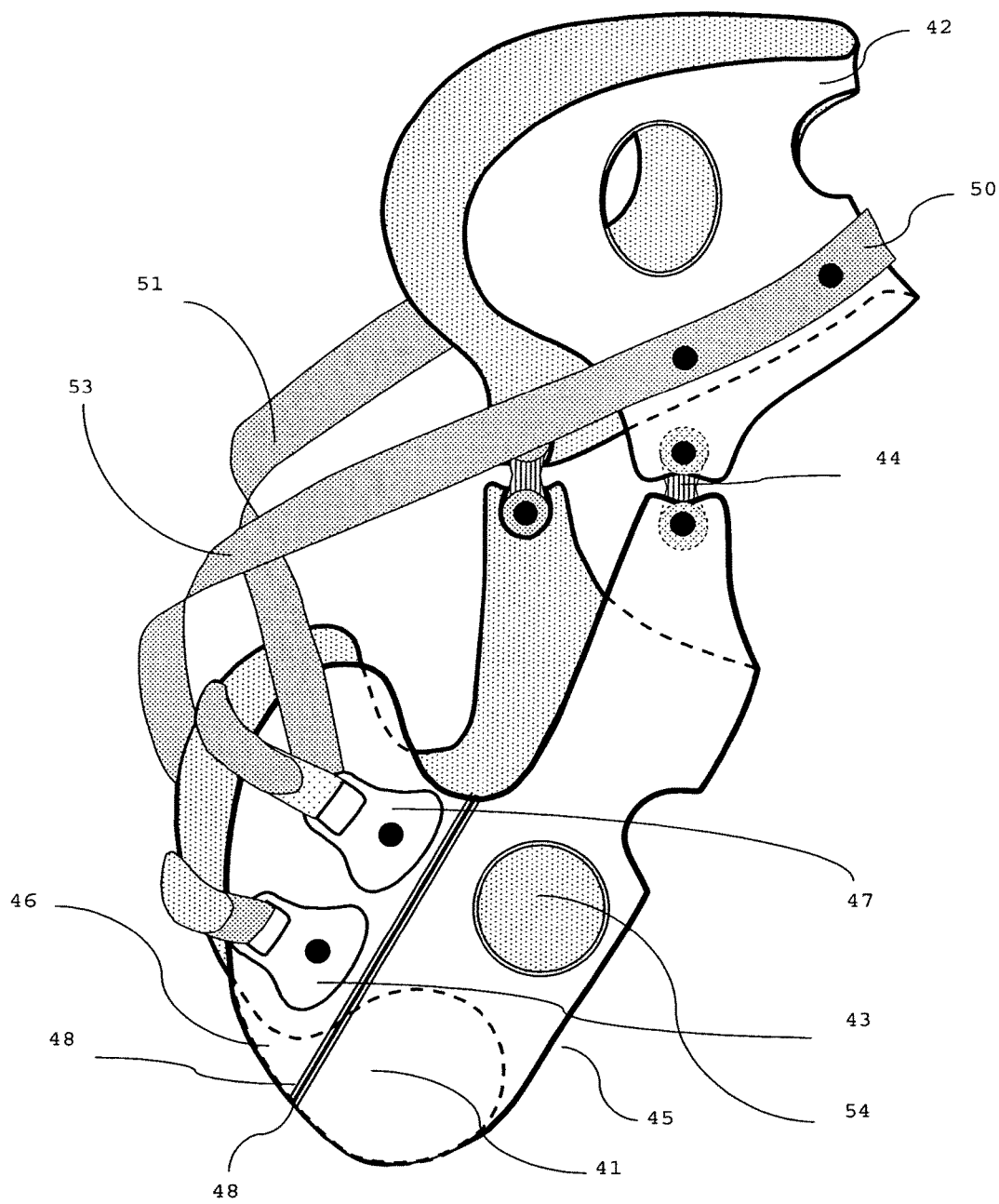
FIG. 3 shows an alternative design of an elbow orthosis according to the invention.
Figure 4:
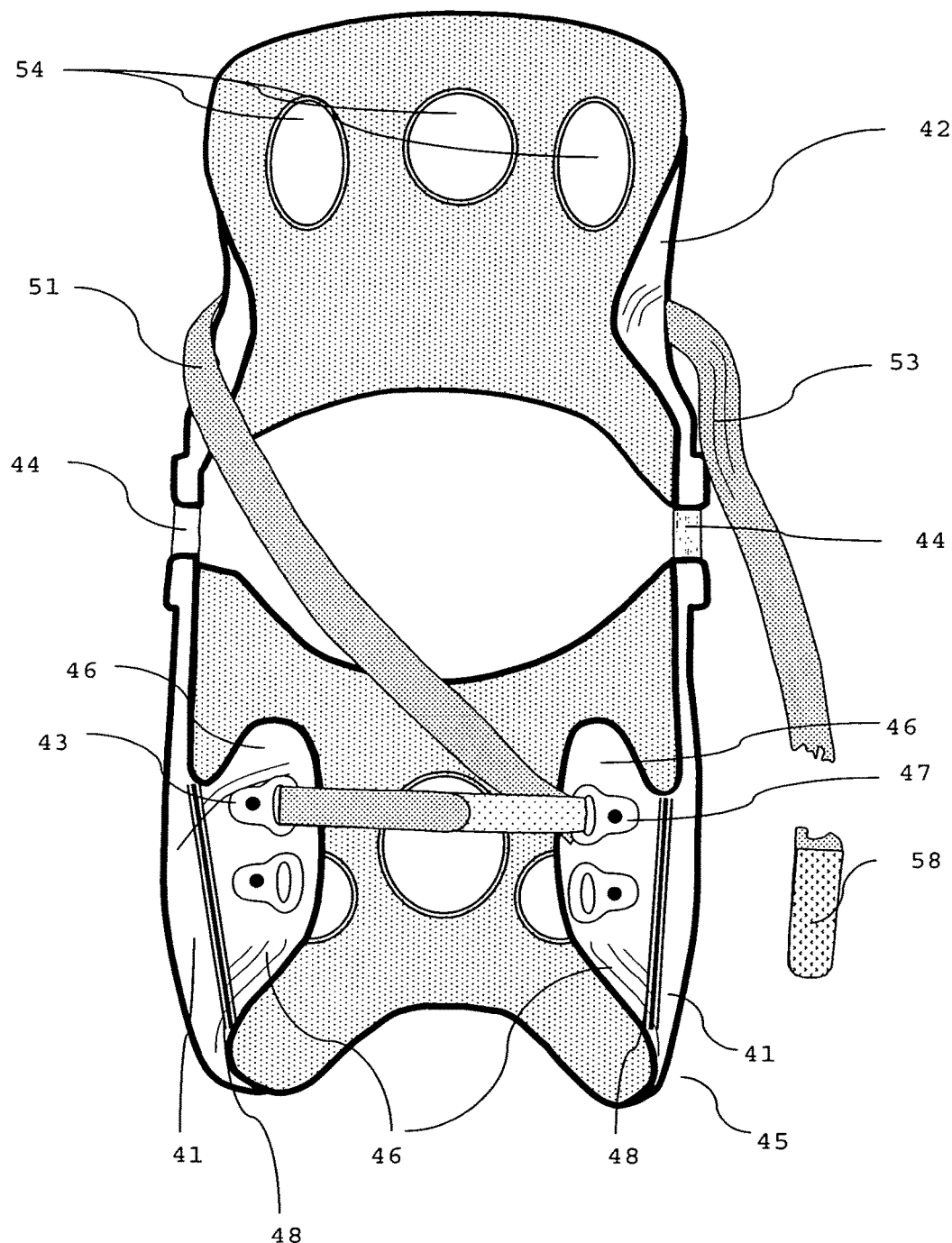
FIG. 4 shows a front view of the orthosis according to FIG. 3.
Figure 5:
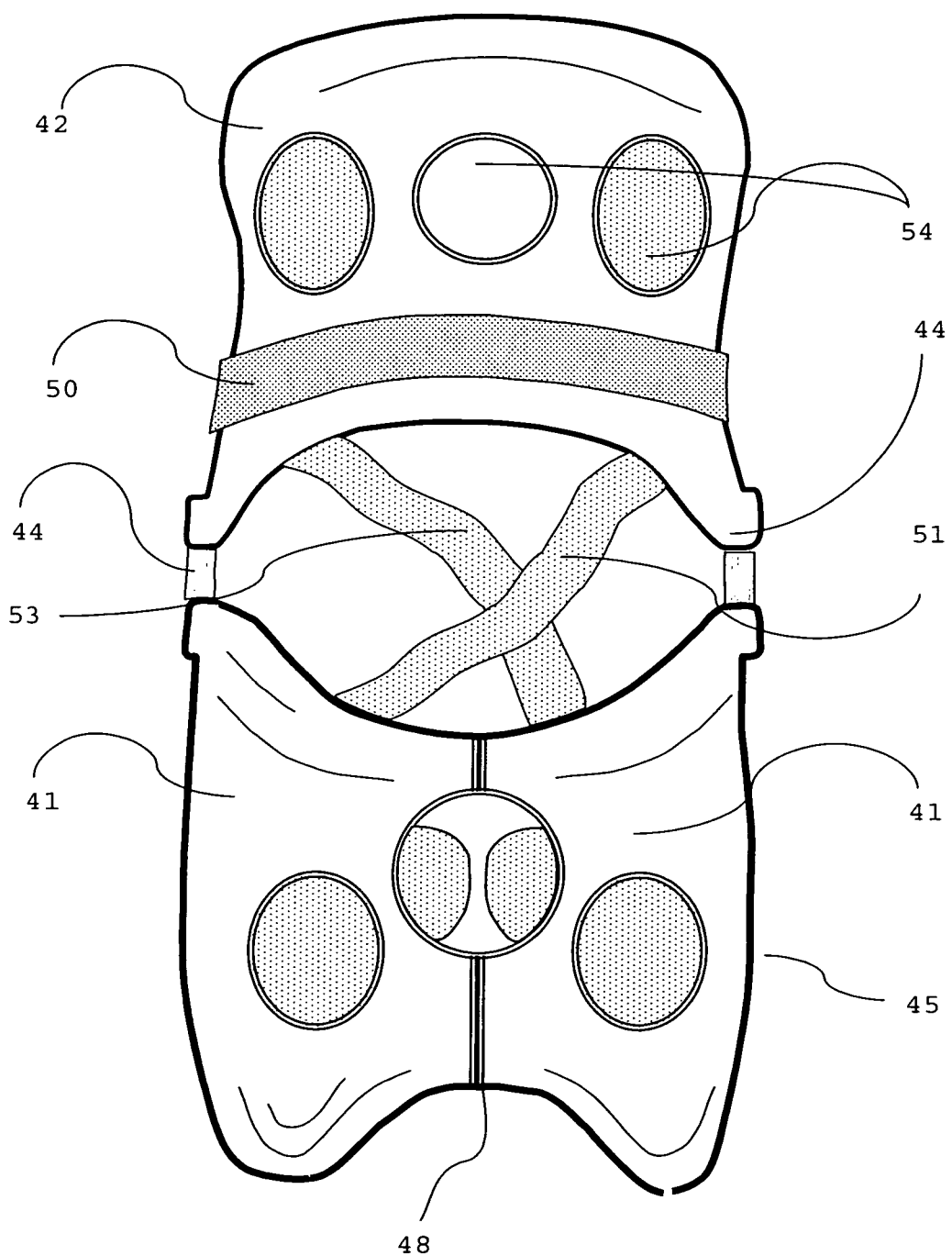
FIG. 5 shows a rear view of the orthosis according to FIG. 1 or 3.

FIG. 5 shows a rear view of an embodiment which is an alternative to FIGS. 1 and 3 and in which the cuff is interrupted substantially at the center, and transverse to the circumference, by a bead or a film hinge (48), which connects the two hard-shell halves (41) to each other flexibly and in an articulated manner. In this embodiment, it is possible to dispense with the separate formation of flexible portions (46) in the area of the pressure-initiating portions (49).

Figure 6A:
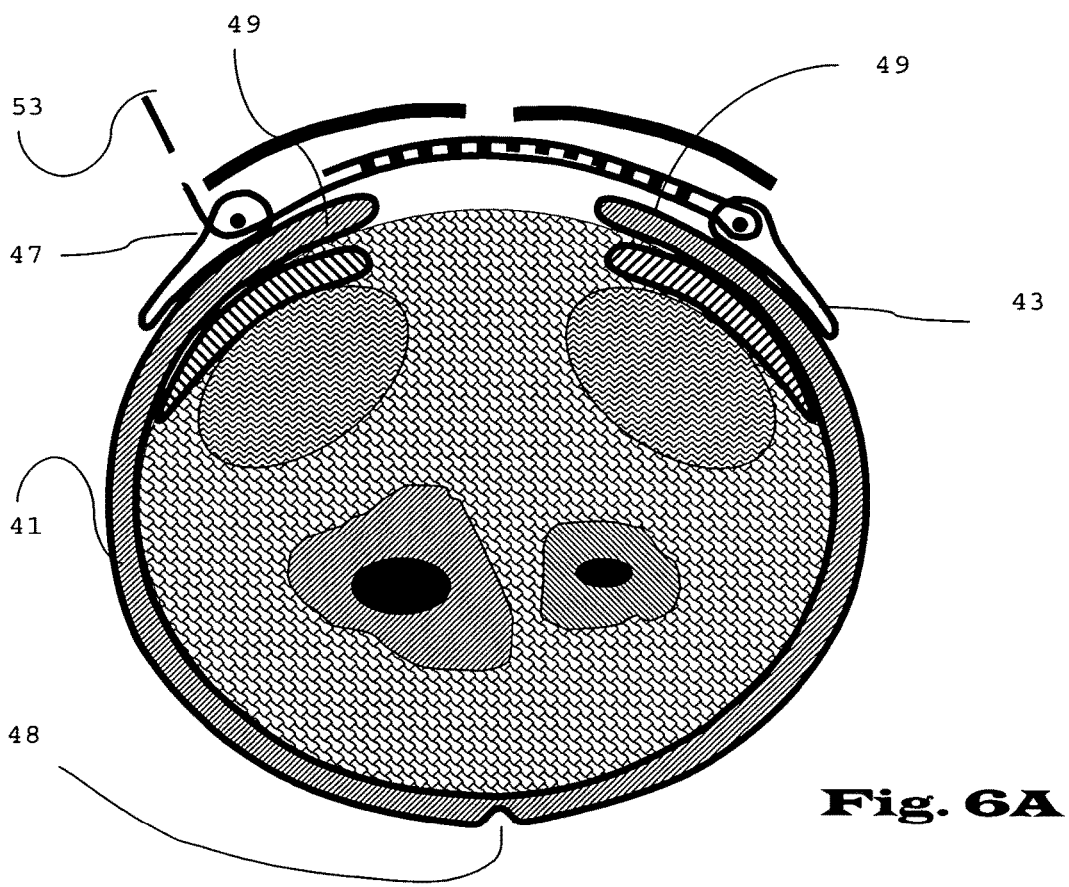
FIGS. 6A, 6B show an anatomical arrangement and functional relationship.
Figure 6B:
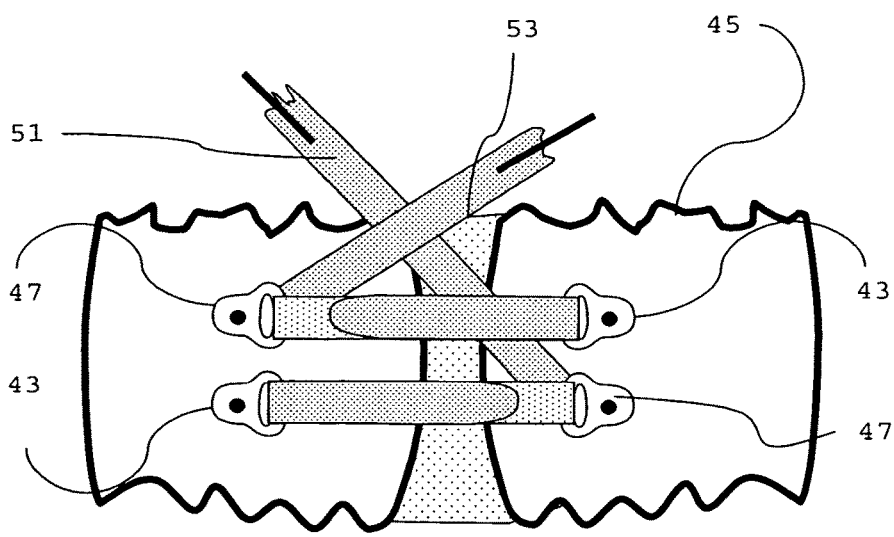

FIG. 6 shows a schematic view of the anatomical arrangement (FIG. 6A) and the functional relationship of a compression of the soft-tissue part imparted by, for example, the tensioning band end (53). In the embodiment shown, the cuff (45) has two substantially non-flexible halves (41), which are connected movably to each other in an articulated manner via a bead (48). Underneath the anchoring points (43) and the tension diverters (47), pads or pressure cushions (49) are arranged (FIG. 6B), by means of which the compression pressure imparted as far as possible symmetrically by the tension on the tensioning band is imparted to the underlying soft-tissue part (FIG. 6A).

Figure 7:
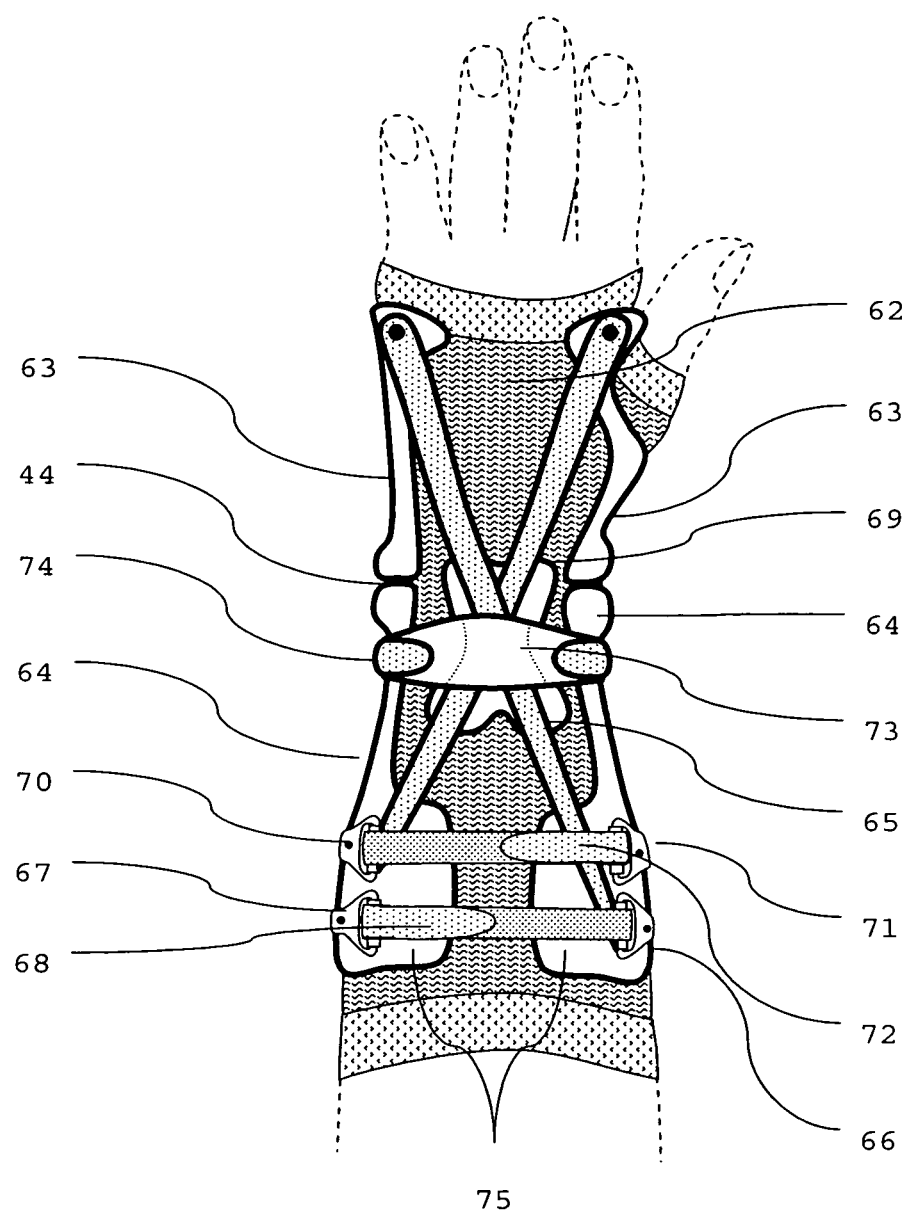
FIG. 7 shows an orthosis according to the invention designed as a wrist orthosis for flexion damping.
Figure 8:
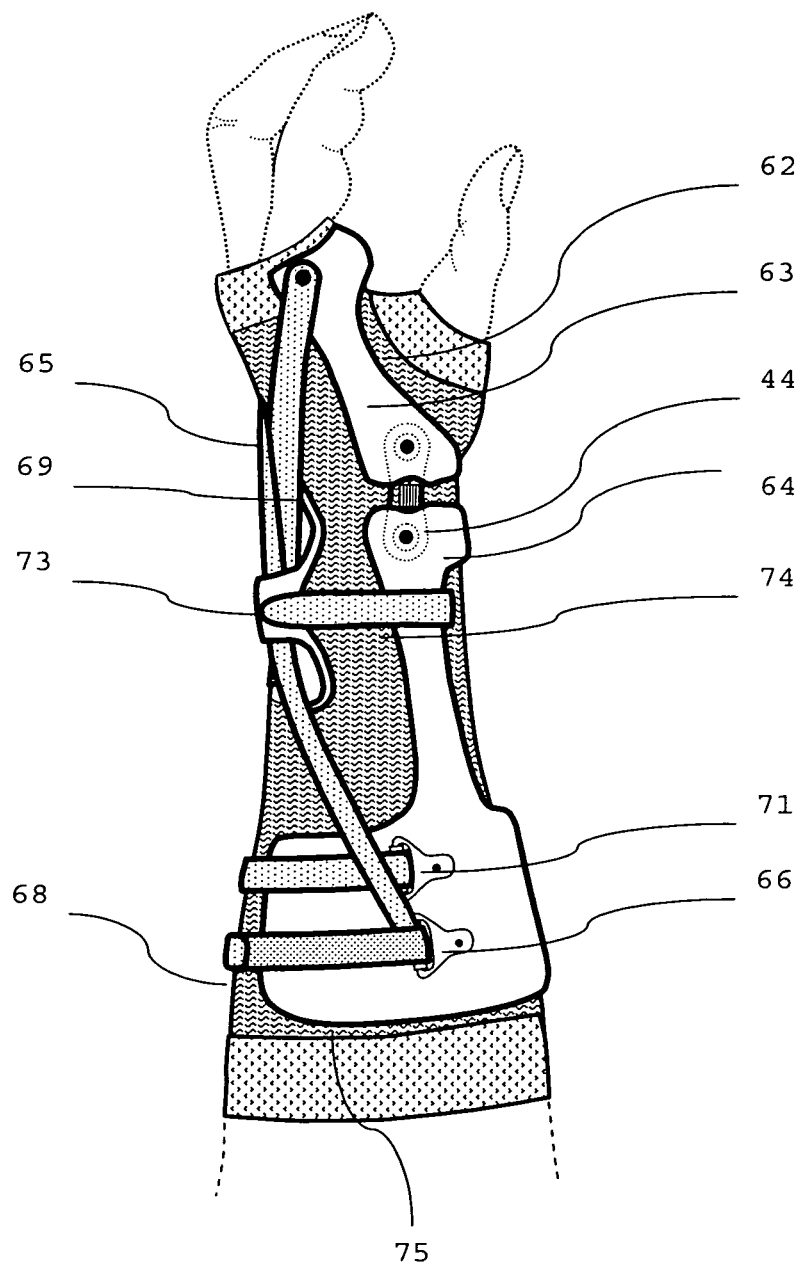
FIG. 8 shows an orthosis according to FIG. 6 in a medial view.
Figure 9:
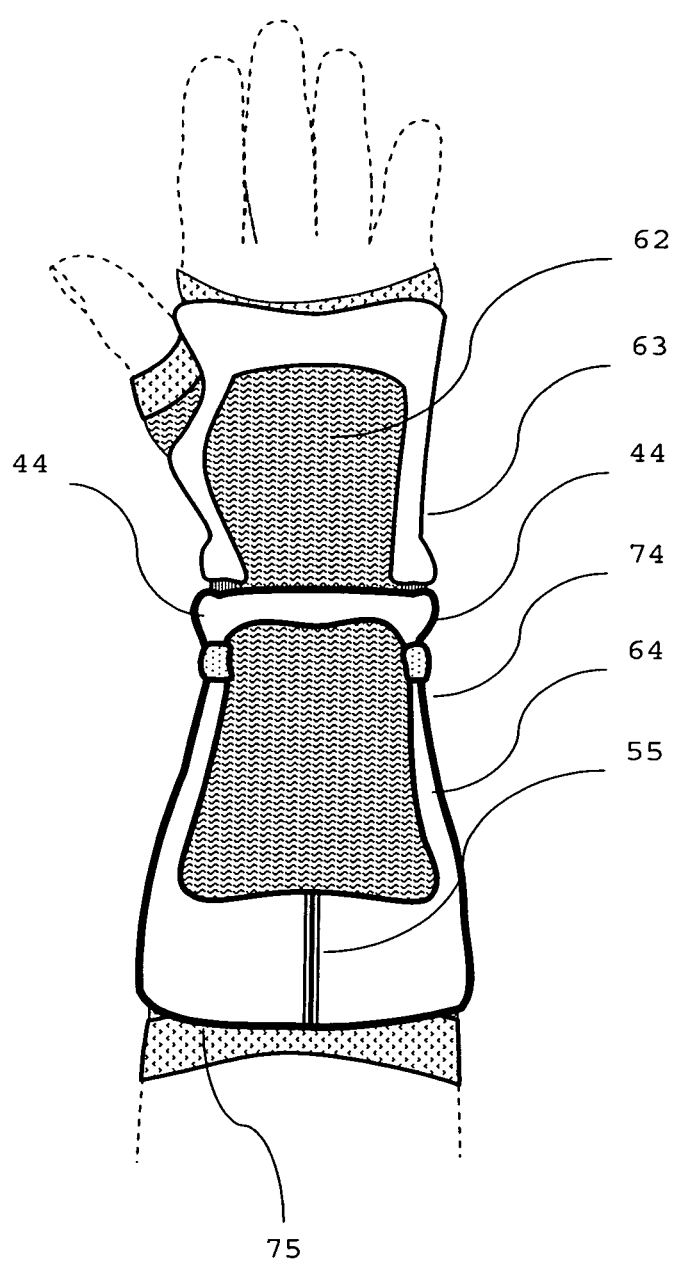
FIG. 9 shows an orthosis according to FIG. 6 in a palmar view.

FIGS. 7, 8 and 9 show dorsal views of a movement-limiting orthosis which is designed for the human wrist and which, on a textile substructure (62), is provided with a frame-like reinforcement (63, 64). In the example shown, it is fitted on the left arm, but it is also conceivable in mirror-inverted form for the right arm. Similar constructions are in principle conceivable for all joints that have a flexion and extension path and that at the same time have compressible muscle bellies located in their proximity.

The orthosis comprises a hand support (63) and a forearm frame (64), which are connected to each other with a force fit by at least one hinge (44), corresponding to the transverse axis of the proximal wrist (radiocarpal joint). The structure composed of hand support (63), forearm frame (64) and hinge (44) is optionally provided on a textile substructure (62).

According to the invention, the movement control is effected by tensile straps (65) and (69) originating from the medial or lateral aspect and crossing each other along their continued extent. The tensile straps (65, 69) originate, on two projections guided from the palmar to dorsal aspect, medially and laterally on the hand support (63). After passing through a for example tubular or tunnel-shaped cover plate (73), and after crossing each other for example in the area of the cover and guide plate (73), each of them is connected to itself, for example by hook-and-loop closures, via the preferred double turn-back. The cover/guide plate can optionally be freely movable or can be displaceably positioned by holding straps (74) on the forearm frame (64).

The hand support (63) originates, for example as a frame, medially at the level of the transverse hinge axis of the wrist, then extends in the distal direction toward the fingers and leaves the thumb sufficient freedom of movement or guides the thumb to the opponents position, runs between thumb and index finger toward the palmar aspect of the hand, extends there from the metacarpophalangeal joint of the index finger along the other metacarpophalangeal joints to the little finger, in so doing takes account, in the section along the metacarpophalangeal joints, of the need for flexion of the long fingers, then, after changing direction, returns laterally as a frame toward the forearm, back to the lateral output of the transverse proximal axis of the wrist. At the output point of the anatomical transverse axis of the proximal wrist joint, flexible articulations are fitted, which produce the articulated connection between hand support (63) and forearm frame (64).

The forearm frame (64) originates, for example medially, at the level of the transverse hinge axis of the proximal wrist, then extends onward in the proximal direction where, on the front aspect of the forearm, it forms, together with its opposite side, a clamp (75) that is open on the front along a quarter of its circumference and is closed on the rear along three quarters of its circumference. On the medial aspect of the forearm, the forearm frame (64) can, at two locations on the rear face of the arm, establish a fixed frame connection to its opposite side on the lateral aspect. One of these connections represents, proximally, the rear face of the already mentioned three-quarter clamp (75). The other transverse connection is a medio-lateral reinforcement strut situated near the joint. The flexible articulations (44), which produce the articulated connection to the hand support (63), are formed on the medial and lateral aspects of this strut. The clamp (75), as part of the forearm frame (64), is optionally provided on the rear face with a rounded V-shaped bead (55), also serving as a flexible articulation for the clamp. This bead is necessary only if the material used for the forearm frame (64) is so stiff that, without such a V-shaped bead (55) acting as a hinge-like groove, a movement in the sense of the opening and closing or the widening and narrowing of the clamp would not be possible. By permitting a greater angle of opening of the clamp (75), the V-shaped bead (55) can also serve to make it easier to fit the orthosis on the arm. The clamp (75), as part of the forearm frame (64), is provided on the front face with several deflection rollers (65, 66, 70, 71). These receive the tensioning straps coming from the hand and crossing over the forearm, and they change the direction of the tensioning straps or deflect them in such a way that, after the reversal of direction, each of the tensioning straps can be connected to itself.

If the hand is flexed at the wrist by external forces, the origins of the two tensioning straps (65, 69) shift around the rotation point of the transverse axis of the wrist in such a way that they exert a tensile stress on the remaining course of the tensioning straps (65, 69). These tensioning straps (65, 69) can follow the movement from this tensile stress only to the extent permitted by their deflection rollers (66, 67) and (70, 71) and by their attachment to themselves and to the tongues of the clamp (75). These elements, however, only allow movement in the tensioning straps when the forearm clamp (75) is at the same time compressed radially against the underlying muscle mass. Therefore, the muscle mass in the forearm of the person concerned is temporarily compressed and at the same time offers an anatomical substrate as damping means, which counteracts the flexion of the wrist.

Figure 10:
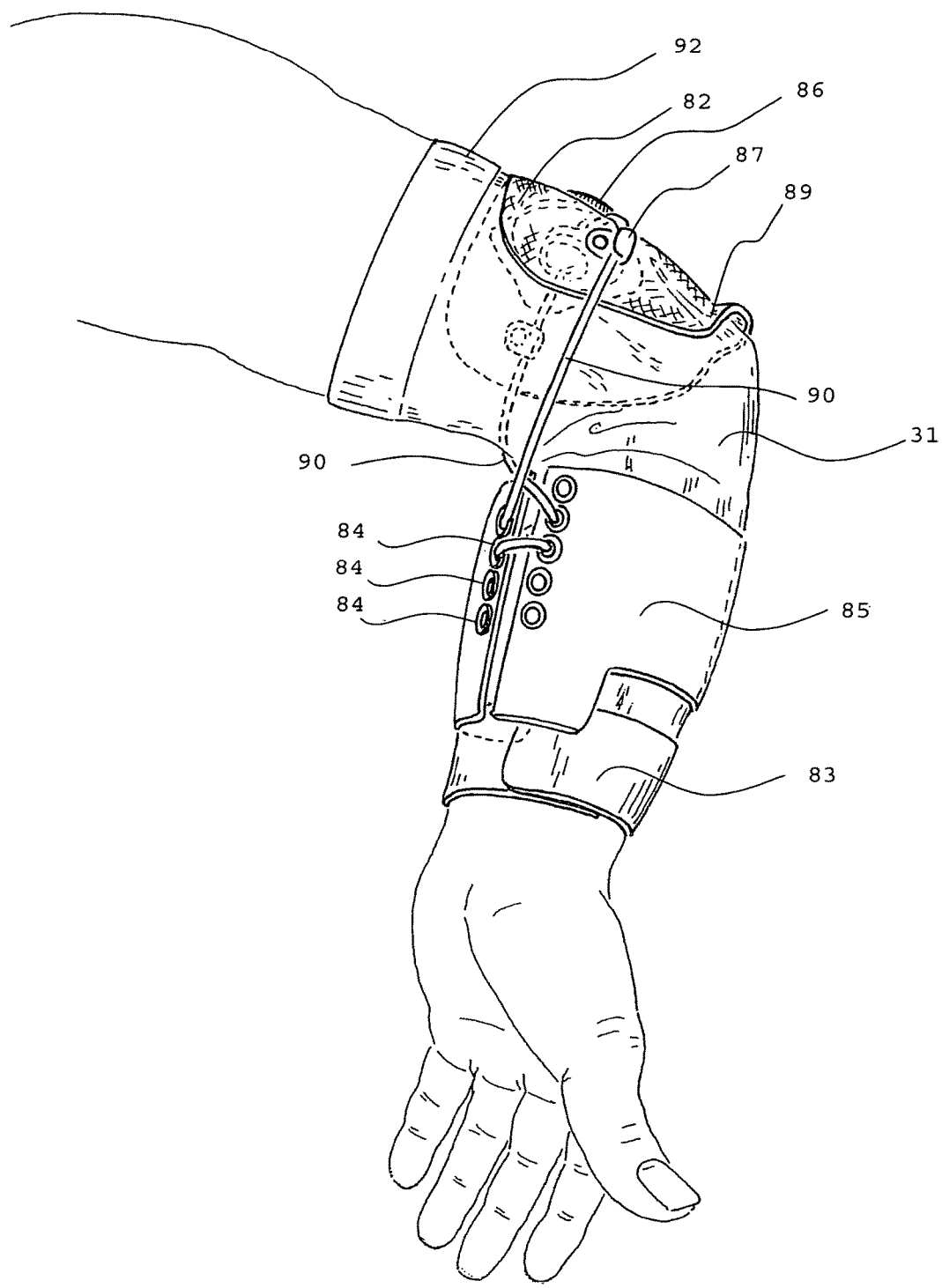
FIGS. 10 and 11 show an alternative design of an elbow orthosis according to the invention.
Figure 11:
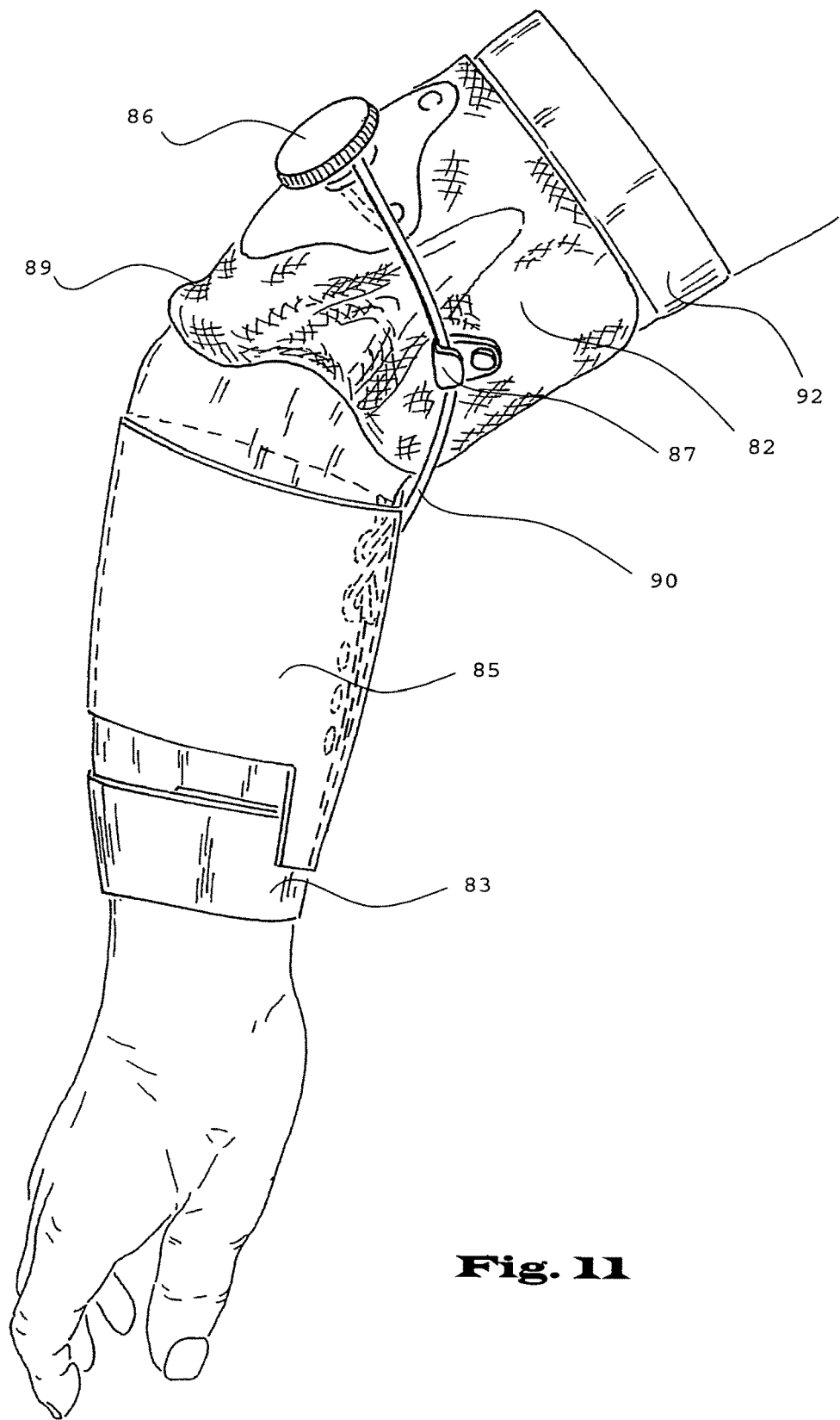

FIGS. 10 and 11 show an alternative embodiment of an elbow orthosis according to the invention. On the textile, stocking-shaped knit (31), above (proximal to) the elbow joint, a substantially non-deformable abutment shell (82) is provided, in particular connected thereto by a hook-and-loop arrangement or by buttons, or welded to the knit to form a unit. Starting from a central clamp mechanism (86), a tensioning band (90) designed as a tensioning cable runs both medially and laterally, extends past the elbow joint to a lower (distal) cuff (85) and is anchored there via tension-deflecting eyelets (84) on the lower cuff (85). In the design shown, a tensioning cable deflector (87) is additionally provided both laterally and medially on the abutment shell (82). A condyle bed (89) is formed both laterally and medially on the abutment shell (42) above the joint condyles. A clamp mechanism (86) for the tensioning cable (90) is designed as a roll-up mechanism with lock on the abutment shell (82). The medial portion and lateral portion of the tensioning cable (90) cross each other in the area of the elbow joint and lead to the lower cuff (85). The lower cuff (85) is likewise designed as a non-deformable shell, which engages substantially round the forearm. It is provided on the knit (31) and connected to the latter by a hook-and-loop arrangement or welded thereto to form an integral unit. A lower holding strap (83) additionally provided on the knit (31) can be placed round the forearm in order to permit a better fit and to safeguard against the knit (31) slipping. An adhesive strap (92) is optionally provided, at least on the upper end of the knit (31). This adhesive strap (92) is provided with an adhesive material, in particular silicone, facing the upper arm, in order to avoid the knit slipping on the upper arm.

The invention claimed is:

1. Orthosis for damping or limiting the movement of a forearm of a patient below an elbow of the patient relative to an upper arm of the patient above the elbow, the forearm being distal to the elbow and defining a distal part of a limb and the upper arm being proximal to the elbow and defining a proximal part of the limb, movement of the forearm resulting in extension of the forearm, the orthosis comprising:
   a shell-shaped cuff configured to be placed on and engage circumferentially around at least three quarters of a total circumference of the forearm of the patient, the shell-shaped cuff having two opposite openings through which the forearm is received when the shell-shaped cuff is placed on the forearm;
   an abutment configured to be placed on and applied to the upper arm, the shell-shaped cuff is coupled to the abutment;
   a tensioning band that extends from the abutment to the shell-shaped cuff and is connected to the abutment and to the shell-shaped cuff with a force fit when the shell-shaped cuff and the abutment are placed on the forearm and the upper arm respectively; and
   the shell-shaped cuff has at least two mutually opposite first and second pressure-initiating portions, each pressure-initiating portion forming a respective part of the shell-shaped cuff that engages circumferentially around at least three quarters of the total circumference of the forearm of the patient, each pressure-initiating portion having a terminating end, the terminating ends of the first and second pressure-initiating portions remaining free when the shell-shaped cuff engages circumferentially around at least three quarters of the total circumference of the forearm of the patient, each pressure-initiating portion having a tension diverter, or a tension-deflecting eyelet, that receives the tensioning band;
   wherein the tensioning band extends crosswise from the abutment to the at least two mutually opposite pressure-initiating portions of the shell-shaped cuff; and
   wherein each of the at least two mutually opposite pressure-initiating portions is integrated with the tensioning band, and the tensioning band is connected between the shell-shaped cuff and the abutment to cause movement of at least one of the at least two mutually opposite pressure-initiating portions to press on an underlying soft-tissue area of the forearm to dampen or to limit the elbow movement when the orthosis is placed on the forearm and on the upper arm.

2. Orthosis according to claim 1, wherein the tensioning band is connected releasably to the shell-shaped cuff in the area of the at least two mutually opposite pressure-initiating portions and the tensioning band can be adjusted in its effective length.

3. Orthosis according to claim 1, wherein the shell-shaped cuff and/or the abutment are provided on a textile knit.

4. Orthosis according to claim 3, wherein at least one of the shell-shaped cuff and the abutment is an integral part of the textile knit.

5. Orthosis according to claim 1, wherein the tensioning band, when the orthosis is placed on the forearm and the upper arm, extends from the abutment above the elbow, on one side of the limb, crosses a longitudinal axis of the limb, extends below the elbow, ends on an opposite side of the limb in the area of the at least two mutually opposite pressure-initiating portions of the shell-shaped cuff.

6. Orthosis according to claim 1, wherein the tensioning band extends from the abutment.

7. Orthosis according to claim 1, wherein each pressure initiating portion has a tension diverter, wherein each tension diverter has an eyelet, and wherein the tensioning band has portions that are laced through the eyelets of the tension diverters whereby the tensioning band is integrated with each respective tension diverter of each one of the at least two mutually opposite pressure-initiating portions to cause movement of at least one of the at least two mutually opposite pressure-initiating portions to press on an underlying soft-tissue area of the forearm to dampen or to limit the elbow movement when the orthosis is placed on the forearm and on the upper arm.

8. Orthosis according to claim 1, wherein the shell-shaped cuff and the abutment are coupled flexibly with a force fit.

9. Orthosis according to claim 1, wherein the abutment comprises the tensioning band encircling the limb above the elbow.

10. Orthosis according to claim 1, wherein the shell-shaped cuff has a lower, non-deformable portion and has an upper, flexible portion on which the at least two mutually opposite pressure-initiating portions are formed.

11. Orthosis according to claim 1, wherein the tensioning band is comprised of an inelastic flexible material.

12. Orthosis according to one of claim 1, wherein the tensioning band is comprised of an elastic material.

13. Orthosis according to claim 1, wherein the tensioning band comprises either completely or partially a tensioning cable.

14. Orthosis according to claim 1, wherein each pressure initiating portion has a tension-deflecting eyelet, and wherein the tensioning band has portions that are laced through the tension-deflecting eyelets whereby the tensioning band is integrated with each respective tension-deflecting eyelet of each one of the at least two mutually opposite pressure-initiating portions to cause movement of at least one of the at least two mutually opposite pressure-initiating portions to press on an underlying soft-tissue area of the forearm to dampen or to limit the elbow movement when the orthosis is placed on the forearm and on the upper arm.

15. Orthosis according to claim 1, wherein the pressure initiating portions are connectable at at least two, spaced locations to even out the movement of the pressure initiating portions.

* * * * *